(12) United States Patent
Da Madice et al.

(10) Patent No.: US 9,586,062 B2
(45) Date of Patent: Mar. 7, 2017

(54) LOW FREQUENCY ULTRASOUND DEVICE WITH COMPUTER-CONTROLLED MONITORING

(71) Applicant: Eurocomponents, Inc., Ormond Beach, FL (US)

(72) Inventors: Lorenzo Da Madice, Daytona Beach, FL (US); Dina Da Madice, Daytona Beach, FL (US)

(73) Assignee: Eurocomponents, Inc., Ormond Beach, FL (US)

( * ) Notice: Subject to any disclaimer, the term of this patent is extended or adjusted under 35 U.S.C. 154(b) by 43 days.

(21) Appl. No.: 14/791,546

(22) Filed: Jul. 6, 2015

(65) Prior Publication Data

US 2017/0007851 A1    Jan. 12, 2017

(51) Int. Cl.
*A61N 7/00*    (2006.01)

(52) U.S. Cl.
CPC ........ *A61N 7/00* (2013.01); *A61N 2007/0034* (2013.01); *A61N 2007/0073* (2013.01)

(58) Field of Classification Search
CPC .............................. A61N 7/00; A61H 23/0245
See application file for complete search history.

(56) References Cited

U.S. PATENT DOCUMENTS

| | | |
|---|---|---|
| 5,549,544 A | 8/1996 | Young et al. |
| 6,666,860 B1 * | 12/2003 | Takahashi ...... A61B 17/320068 606/34 |
| 7,431,704 B2 | 10/2008 | Babaev |
| 8,226,582 B2 | 7/2012 | de Ana et al. |
| 8,376,969 B2 | 2/2013 | Babaev |
| 2003/0023193 A1* | 1/2003 | Soring ............ A61B 17/22004 601/2 |
| 2003/0097054 A1* | 5/2003 | Sasaki ...................... A61B 8/00 600/407 |
| 2004/0230116 A1* | 11/2004 | Cowan ............... A61B 17/2202 600/437 |
| 2005/0085875 A1* | 4/2005 | Van Zuylen ......... A61N 5/0616 607/88 |
| 2007/0123780 A1 | 5/2007 | Wu |
| 2007/0239041 A1* | 10/2007 | Chatterjee .......... A61B 5/02152 600/490 |
| 2007/0299369 A1 | 12/2007 | Babaev |
| 2009/0118651 A1* | 5/2009 | Rousso .................. A61H 11/00 601/134 |

(Continued)

FOREIGN PATENT DOCUMENTS

WO    2009085241 A2    6/2009
WO    2010101532 A1    9/2010

*Primary Examiner* — Thomas J Sweet
*Assistant Examiner* — Hien Nguyen
(74) *Attorney, Agent, or Firm* — Nancy J. Flint, Esq.; Nancy J. Flint, Attorney At Law, P.A.

(57) ABSTRACT

An ultrasound device for therapeutic and aesthetic treatment is disclosed. Different types of hand probes used with the device produce different effects within biological tissues. The device can operate at low frequencies of around 20 KHz to 100 KHz. The device can be operated in continuous mode or pulsed mode with different duty cycles. Software and hardware is used to control power output of the hand probes; treatment time; to perform diagnostics of the hand probes; and to shut off ultrasound emissions in the case of abnormal or incorrect functioning of the hand probes.

18 Claims, 18 Drawing Sheets

(56) References Cited

U.S. PATENT DOCUMENTS

| | | |
|---|---|---|
| 2010/0137752 A1 | 6/2010 | Heine et al. |
| 2013/0006153 A1 | 1/2013 | Lewis, Jr. |
| 2013/0289416 A1 | 10/2013 | Feferberg |
| 2014/0228721 A1* | 8/2014 | Ehrenreich ........ A61H 23/0245 601/47 |
| 2014/0257146 A1 | 9/2014 | Kost et al. |
| 2014/0316310 A1* | 10/2014 | Ackermann ....... A61N 1/36046 601/46 |
| 2015/0148664 A1* | 5/2015 | Stolka ................. A61B 8/4254 600/424 |

* cited by examiner

LOW FREQUENCY ULTRASOUND DEVICE WITH COMPUTER-CONTROLLED MONITORING

FIELD OF THE INVENTION

The invention relates to an ultrasound device for therapeutic and aesthetic treatment. Different types of hand probes used with the device produce different effects within biological tissues. The device can operate at low frequencies of around 20 KHz to 100 KHz. The device can be operated in continuous mode or pulsed mode with different duty cycles. Software and hardware is used to control power output of the hand probes; treatment time; to perform diagnostics of the hand probes; and to shut off ultrasound emissions in the case of abnormal or incorrect functioning of the hand probes.

BACKGROUND OF THE INVENTION

Ultrasonic energy is a powerful generator of biological effects. There are three primary benefits to ultrasound. The first is the speeding up of the healing process from an increase in blood flow in a treated area. The second is a decrease in pain from reduction of swelling and edema. The third is gentle massage of muscles tendons and/or ligaments in a treated area because no strain is added and any scar tissue is softened.

Therapeutic ultrasound provides two main effects: thermal and non-thermal. Thermal effects are due to the absorption of the sound waves. Non thermal effects are from cavitation, microstreaming and acoustic streaming. Cavitational effects result from the vibration of tissue causing microscopic bubbles to form, which transmit vibrations in a way that directly stimulates cell membranes. This physical stimulation appears to enhance the cell-repair effects of the inflammatory response. Therapeutic applications of ultrasonic heating utilize longer durations of heating with unfocused beams, or utilize higher intensity than diagnostic ultrasound. The use of unfocused heating, for example in physical therapy to treat highly absorbing tissues such as bone or tendon, can be moderated to produce enhanced healing without injury.

Ultrasound is applied using a transducer or hand probe that is in direct contact with the patient's skin. Gel is used on the surfaces of the head of the hand probe to reduce friction and assist transmission of the ultrasonic waves. Therapeutic ultrasound in physical therapy is alternating compression and rarefaction of sound waves with a frequency of >20,000 cycles/second. Therapeutic ultrasound frequency used is generally 0.7 to 3.3 MHz.

Maximum energy absorption in soft tissue occurs from 2 to 5 cm. Intensity decreases as the waves penetrate deeper.

Conditions for which ultrasound may be used for treatment include the following examples: ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion.

Study has shown that ultrasound helps in enhancing the metabolic activities of cells, thus helping in tissue repair, especially in soft tissue injuries.

U.S. Pat. No. 7,431,704 to Babaev et al. and titled Apparatus and Method for the Treatment of Tissue with Ultrasound Energy by Direct Contact, discloses an apparatus and method for the treatment of tissue, such as hard and soft tissues, wounds, tumors, muscles, and cartilage, through the direct contact of ultrasound energy. See Abstract. Ultrasound energy is delivered to a target area through direct contact with an ultrasound tip. Ultrasound energy is also delivered through direct contact with a coupling medium. The ultrasound tip is specially designed to comprise of a cavity area for controlled fragmentation and the simultaneous sonication of a target area. The specially designed ultrasound tip allows for ultrasound energy to focus on a target area. The ultrasound apparatus may be moved in a variety of different directions during the treatment of tissue.

U.S. Patent Appln. Publn. No. 20070299369 also to Babaev et al. and titled Ultrasound Wound Care Device and Method, discloses an ultrasound device and method for treating wounds. The ultrasound wound care device comprises a generator, an ultrasound transducer, an ultrasound horn, and a cavitation chamber. The device may further comprise a fluid, non-atomized, coupling medium. Ultrasound titled Low- and Mid-Frequency Ultrasound Device with Enhanced Cavitation Effect in Combination with Radial In-Depth Skin Therapy, discloses a device for treatment of subcutaneous fat cells, specifically to a device that uses low- and mid-frequency ultrasound waves in combination with radial deep skin therapy. A low- and mid-frequency focused ultrasound device for cavitation in combination with radial deep therapy that comprises a handle (1), a fastening ring (3), a bell-shaped housing (2), an ultrasound source and a vacuum pump, characterized in that low-frequency ultrasound cavitation therapy is performed simultaneously with vacuum therapy with a skin fold, and additionally characterized in that excess gel is removed via a filtration system in the handle.

BRIEF SUMMARY OF THE INVENTION

The invention relates to an ultrasound device for therapeutic and aesthetic treatment. Different types of hand probes used with the device produce different effects within biological tissues. The device can operate at low frequencies of around 20 KHz to 100 KHz as well as higher frequencies as high as 3 MHz. The device can be operated in continuous mode or pulsed mode with different duty cycles. Software and hardware is used to control power output of the hand probes; treatment time; to perform diagnostics of the hand probes; and to shut off ultrasound emissions in the case of abnormal or incorrect functioning of the hand probes.

DETAILED DESCRIPTION OF THE INVENTION

Figures 1A, 1B, 1C:
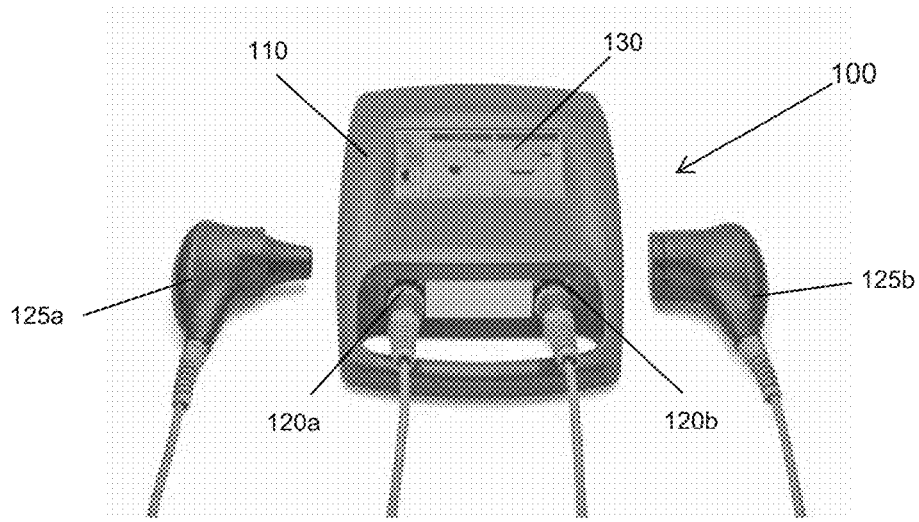
FIG. 1A depicts one embodiment of the low frequency ultrasound device with computer-controlled monitoring.
FIG. 1B depicts a view of one embodiment of a hand probe.
FIG. 1C depicts a view of a second embodiment of a hand probe.

The invention relates to an ultrasound device for therapeutic and aesthetic treatment. Different types of hand probes used with the device produce different effects within biological tissues. The device can operate at low frequencies of around 20 KHz to 100 KHz as well as higher frequencies as high as 3 MHz. The device can be operated in continuous mode or pulsed mode with different duty cycles. Software and hardware is used to control power output of the hand probes; treatment time; to perform diagnostics of the hand probes; and to shut off ultrasound emissions in the case of abnormal or incorrect functioning of the hand probes.

In one embodiment, the device comprises a main unit/generator and transducers/hand probes comprising one or more piezoelectric elements which are used for both therapeutic treatment of humans, dogs, horses or other large animals and aesthetic medicine treatments aimed at body contouring, skin rejuvenation or for the treatment of inflammatory skin conditions (e.g., acne, psoriasis, etc.). In one embodiment the piezoelectric elements are piezoelectric crystals and in one embodiment the piezoelectric elements are piezoelectric ceramic disks.

The main unit/generator can be used with different types of hand probes, which produce different effects within biological tissues. The piezoelectric elements in the hand probes are excited by a sinusoidal voltage with nominal frequency ranging from 20 KHz to 3 MHz.

The lower the ultrasound frequency, the deeper the ultrasound physiological effects through biological tissues. The higher the ultrasound frequency, the more superficial the ultrasound physiological effects through biological tissues. Therefore by operating at different ultrasound frequencies it is possible to selectively treat specific areas of the body at different depths.

Hand probes transform electrical energy into acoustic pressure waves. The electro-acoustic hand probes are electrically stimulated by the generator and emit an acoustic wave at ultrasonic frequency (which can be from 20 kHz to 3 MHz), which propagates in the area to treat.

The transduction from electric wave to pressure wave is possible due to piezoelectric elements which operate inside the hand probes. During operation of the device these piezoelectric elements are electrically stimulated and deformed. These contractions and dilations, caused by the applied sinusoidal tension, produce the desired ultrasonic wave.

The ultrasonic wave produced by the piezoelectric elements propagates by direct contact toward a sonotrode on one side and toward a steel plate on the other side. Due to its nature, the steel plate blocks the ultrasonic wave propagation and prevents radiation from propagating toward the cover and the operator of the device. All emitted energy from the piezoelectric elements is thus directed toward the sonotrode which applies the ultrasonic energy to the transducer contact surface.

Hand probe models can differ for the transducer contact surface shape, diameter and emission type. The transducer contact surface shape can be flat, concave or convex, or any other shape that can best adapt/couple to the surface to treat. Different shapes in the ultrasound transducer contact surface determine also the type of ultrasound radiation and intensity emitted:

Flat hand probes feature a collimated beam, which spreads minimally as it propagates through biological tissues. Flat hand probes are used for the treatment of large/flat areas.

Concave hand probes feature a focused beam which leads to more intense and deeper ultrasound effects. Concave hand probes are used for ultrasound application on rounded areas of the body (e.g. knees, elbows, etc.).

Convex hand probes feature a divergent beam to apply ultrasound on wide areas. Convex hand probes can better adapt to certain body areas.

It is important to have good coupling between the hand probe transducer and the surface to treat, since air is not conductive for ultrasounds. Therefore, the better the hand probe adhesion to the skin, the better the ultrasound propagation through tissues.

The transducer contact surface can have different diameters or dimensions. For example, smaller diameter hand probes can be employed to treat human faces for skin rejuvenation, while very large diameter hand probes can be employed for therapeutic treatment on equine backs.

Ultrasonic emission can be continuous or pulsed with different duty cycles. Continuous emission ultrasound mainly generates diathermy/heat within biological tissues. This treatment modality is usually employed for pathologies in the chronic phase or when heat is a desirable element (for example to increase soft tissue extensibility before active or passive stretching activities). Superficial heat can stimulate collagen production for skin rejuvenation treatments.

In the pulsed emission modality the ultrasound wavetrain is interrupted at specific intervals (duty cycle). Pauses in the wavetrain occur to promote intense mechanical effects and so that heat can be dissipated by circulation. The mechanical non-thermal effects of ultrasound include: cavitation, acoustical streaming and microstreaming.

Different duty cycles combined with different power outputs can produce stable or unstable cavitation. Pulsed emission modality with stable cavitation is preferred to treat pathologies in the acute phase, when heat is an undesirable factor. Pulsed emission modality with unstable cavitation is employed in aesthetic medicine, where the micro bubbles implosion is used to damage adipocytes for body contouring.

Through dedicated software and hardware the main unit/generator controls power output of connected hand probes, treatment time and performs diagnostics on the connected hand probes. In one embodiment, the software/hardware monitors for correct functioning of the connected hand probes and, in case of abnormal or incorrect functioning of the connected hand probes, automatically shuts off ultrasound emission and sounds an alert to the problem.

The device is controlled by two integrated printed circuit board assemblies, which share information through an encoded and redundant CAN BUS protocol in order to avoid communication errors. A first printed circuit board assembly is the display circuit board assembly (the master) and a second printed circuit board assembly is the power circuit board assembly (the slave). Each printed circuit board assembly comprises a printed circuit board and a plurality of electronic components, such as resistors, capacitors, transistors, diodes, amplifiers, resistor arrays, logic gates, semiconductors, clocks, switches, microprocessors and memory. The display circuit board assembly sends various requests for information and the power circuit board assembly responds to the requests of the display circuit board assembly. The requests include reading hand probe manufacturer information stored in an IC chip inside each hand probe by its manufacturer; calibration of hand probe; power on/off; and frequency parameters. The hand probes are controlled by the power circuit board assembly. For example, and not limiting the invention in any way, the power circuit board assembly regulates if and how much amperage is sent to the hand probes; regulates treatment time; and monitors the hand probe's performance. Hand probe performance and feedback are stored inside the internal memory of the power circuit board assembly. The interaction between the hardware and the software is total and complete, and allows that a hardware failure is detected and managed by the software and similarly that a software failure, or a hardware failure which compromises software functionality, is managed by the hardware. Through continuous communication, the first and second integrated printed circuit board assemblies monitor each other and in case of malfunctioning of either software or hardware in one of the first or second integrated printed circuit board assembly, the other integrated printed circuit board assembly stops the ultrasound emission.

The commands made by the display integrated printed circuit board assembly (master) to the power integrated printed circuit board assembly (slave) comprise:

Reads code device 1 (towards hand probe)
Reads code device 2 (towards hand probe)
Reads buffer 128 bytes eqprom device 1 (towards hand probe)
Reads buffer 128 bytes eqprom device 2 (towards hand probe)
Writes 8 bytes to the address specified on device 1 (towards hand probe)
Writes 8 bytes to the address specified on device 2 (towards hand probe)
Relay ON/OFF (towards relay)
Sends hand probe codes (towards hand probe)
Hand probe calibration (hand probes/current measuring section/power transformer section)
Power ON/OFF (power transformer section)
Sends analog inputs (current measuring section)
Reset current protection occurred (HW primary protection)
Basic and modulating frequency parameters (power transformer section)

In operation, once the main unit/generator detects a hand probe connection, it reads the hand probe's serial number and its basic parameters. If the data supplied to the main unit/generator are adequate, the main unit/generator performs a check of the hand probe characteristics which must be within the parameters set by the manufacturer that have been preloaded into the memory of the device.

In this phase a safety check on the hand probe is performed, which comprises acquiring data relative to the hand probe's performance. The hand probe is brought between 10% and 100% of its nominal power and its characteristics are recorded in 2% increments for 40 data points. For each of the recorded data points, the resonance frequency of the hand probe is identified and amperage demand is checked. If the amperage demand exceeds the maximum amperage recorded inside the hand probe during manufacturing, the user is advised that the hand probe may be dirty, broken or otherwise inoperable, and that treatment cannot be performed using that hand probe.

The hand probe parameters that are transferred stored in the device memory comprise:

hand probe serial number;
month and year of production;
hand probe transducer type (e.g. flat, concave or convex);
hand probe transducer dimensions (e.g. diameter, width, height, depth);
hand probe emission type (continuous or pulsed/duty cycle emission);
hand probe duty cycle parameters;
carrier frequency (it is defined for every power level as the frequency of minimum power absorption);
modulating frequency (the frequency to which the carrier is PWM modulated);
PWM modulating (indicates the PWM modulating percentage of the carrier);
maximum current (it is the maximum current that the hand probe can absorb during normal functioning);
hand probe remaining treatment hours (it indicates the amount of treatment hours available before the hand probe needs to be reconditioned by the manufacturer).

During ultrasound treatment the device compares the hand probe's saved parameters with the actual hand probe's performance. The hand probe is connected to the device via a four prong connector. Two of the prongs deliver power to the piezoelectric element embedded in the hand probe and two of the prongs provide communication between the hand probe and the device for constant monitoring of performance of the hand probe. For example, the device can determine if the hand probe is placed on biological tissue or water because the hand probe's demand for amperage increases due to the highly conductive nature of water to the point it exceeds the predetermined safety limit. The device shuts off power to the hand probe when the safety limit is exceeded and sounds an alarm. In another example, if the piezoelectric element is damaged there will be an abnormal demand for amperage by the hand probe, and if the amperage demand exceeds the predetermined safety limit the device will shut off power to hand probe and sound an alarm. In another example, if the hand probe overheats the piezoelectric element will not freely expand and contract, which is a malfunction that can be detected by the device which causes power to be shut off to the hand probe and an alarm to be sounded.

If any predetermined and programmed limits of the hand probe are exceeded or otherwise not met as determined by the device, the main unit/generator detects the malfunction and shuts off power to the hand probe, thus cutting off ultrasound emission. Similarly, if there is a malfunction in the main unit/generator that could cause the hand probe to overheat during power absorption, the hand probe will not pass the initial test.

The operator can easily verify this safety measure: if the hand probe is pressed onto the body or with fingers while the main unit/generator is engaged in testing/auto-calibration, the main unit/generator detects an abnormal situation and gives an error message.

These operations are automatic and mandatory in order to start a treatment session using the device. During start up the automatic check cannot generate errors, since the programmed protections employed lock the system if there are any deviations in the hand probe's characteristic curve.

The user does not need to perform any calibration tasks, since each individual hand probe is calibrated by the manufacturer with specific parameters depending on the desired physiological effects and patient characteristics (e.g. therapeutic treatment of humans, dogs, horses or other large animals or aesthetic medicine treatments aimed at body contouring or skin rejuvenation).

For safety reasons the manufacturer assigns to each hand probe 500 hours of treatment. When all treatment hours have expired, the hand probe will stop working Each time the main unit/generator detects a hand probe connection, the remaining hours of treatment are displayed on the touch screen. When 20 hours of treatment time are left for a hand probe, the user is reminded by the touch screen to contact an authorized dealer for hand probe re-calibration and refurbishing.

This device presents significant advances in patient and operator safety compared to traditional ultrasound devices:
  hand probe calibration and duty cycle are determined by the manufacturer and stored for each individual hand probe, therefore eliminating the risk of improper calibration by the user, which could lead to tissue damage;
  pre-treatment checks operated by the main unit/generator on connected hand probes prevent that damaged, defective or improperly calibrated hand probes are used to perform a treatment, which can lead to potentially harmful effects;
  the device constantly monitors to prevent hand probe overheating, which can lead to burns and tissue necrosis;
  the 500 hours limit assigned by the manufacturer to each hand probe is an extra precaution to guarantee that the equipment always produces the intended physiological effects within biological tissues, therefore potentially eliminating the risk of undesired effects or tissue damage. If ultrasound manufacturers recommend to periodically return the equipment for inspection and re-calibration, in reality this is not always done and very often units in need of calibration are used, which can lead to harmful effects on tissues.

The equipment can be connected to a grounded outlet or can be battery operated.

The device is intended to apply ultrasonic waves within body tissues for the treatment of selected conditions in either human medicine, veterinary medicine or aesthetic medicine.

A coupling medium (such as ultrasound gel) should always be interposed between the hand probe transducer and the patient skin, in order to facilitate ultrasound propagation through biological tissues.

Therapeutic ultrasound can treat several musculoskeletal conditions, such as soft tissue injuries (muscle, tendon, ligament and joint conditions) and bone pathologies.

In aesthetic medicine ultrasound treatments are mostly aimed at body contouring or skin rejuvenation.

A different version of the device can combine ultrasound to one or more different technologies, such as shock waves, radio frequency, electro-magnetic waves and/or laser therapy. In fact, depending on the pathology to treat, other technologies can aid ultrasound treatments to obtain the desired results (e.g. ultrasound can be combined with radio frequency in physiotherapy treatments or ultrasound can be combined with laser in aesthetic medicine treatments).

The generator/s for auxiliary technologies are housed within the main unit, while the hand pieces can be combined within the ultrasound hand probes or simply can be separated hand pieces connected to the main unit.

Turning to the figures, FIG. 1A depicts one embodiment of the low frequency ultrasound device with computer-controlled monitoring. Device 100 comprises a main unit/generator 110; two hand probe connection inputs 120a, 120b; and a display 130 that displays a variety of information regarding hand probes; the treatment protocol selected; performance parameters; and other information. For example, display 130 may display a security feature to operate the main unit/generator 110, such as a PIN number. FIG. 1B depicts a view of one embodiment of a hand probe 125a having a power cord and a power cord connector, and FIG. 1C depicts a view of a second embodiment of a hand probe 125b having a power cord and a power cord connector.

Display 130 may provide a selection to start the operation of the main unit/generator 110 or to set information such as date, time or treatment parameters such as hand probe 125a, 125b power output and duration of treatment. When hand probe 125a, 125b is attached to main unit/generator 110, display 130 may display features of hand probe 125a, 125b such as face configuration and manufacturer, or whether some parameter of hand probe 125a, 125b is not recognized. Parameters relating to the history of hand probe 125a, 125b may be displayed on display 130, for example the number of hours of treatment left for hand probe 125a, 125b under the manufacturer's guidelines. There may be an indicator on display 130 indicating whether hand probe 125a, 125b is attached to main unit/generator 110. Display 130 may provide an alarm display if hand probe 125a, 125b or main unit/generator 110 malfunctions. Display 130 may also provide display qualities such as contrast and screen color which can be adjusted by the operator of main unit/generator 110. During treatment, parameters such as time and power may be displayed on display 130 and the operator may adjust parameters such as power output from display 130. Main unit/generator 110 further comprises a first integrated printed circuit board assembly and a second integrated printed circuit board assembly (not shown) for controlling the operation of the device 100.

Figures 1D, 1E:
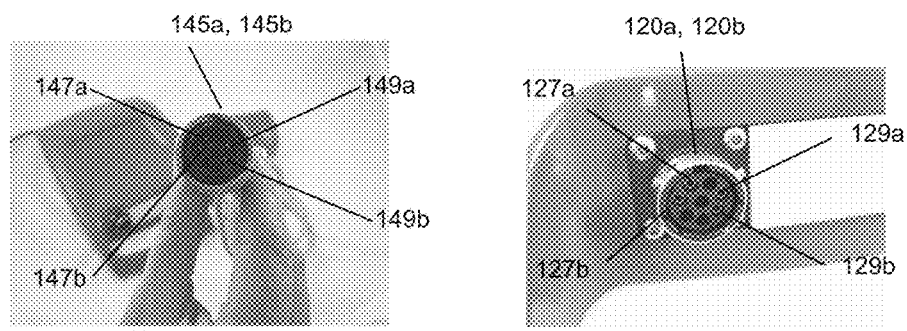
FIG. 1D depicts a view of power cord connector.
FIG. 1E depicts a view of power cord connection inputs.

FIG. 1D depicts a view of power cord connector 145a, 145b comprising 4 prongs 147a, 147b, 149a and 149b.

FIG. 1E depicts a view of power cord connection inputs 120a, 120b comprising 4 inlets 127a, 127b, 129a and 129b. Inlets 127a and 127b allow power to be provided to hand probe 125a, 125b and inlets 129a, 129b allow for constant communication between hand probe 125a, 125b and main unit/generator 110 for constant monitoring of hand probe 125*a*, 125*b*. Power cord connector prongs 147*a*, 147*b* mate with power cord connection input inlets 127*a*, 127*b* to provide power from main unit/generator 110 to hand probe 125*a*, 125*b*. Power cord connector prongs 149*a*, 149*b* mate with power cord connection input inlets 129*a*, 129*b* to provide communication with and monitoring by main unit/generator 110 of hand probe 125*a*, 125*b*.

Figure 2:
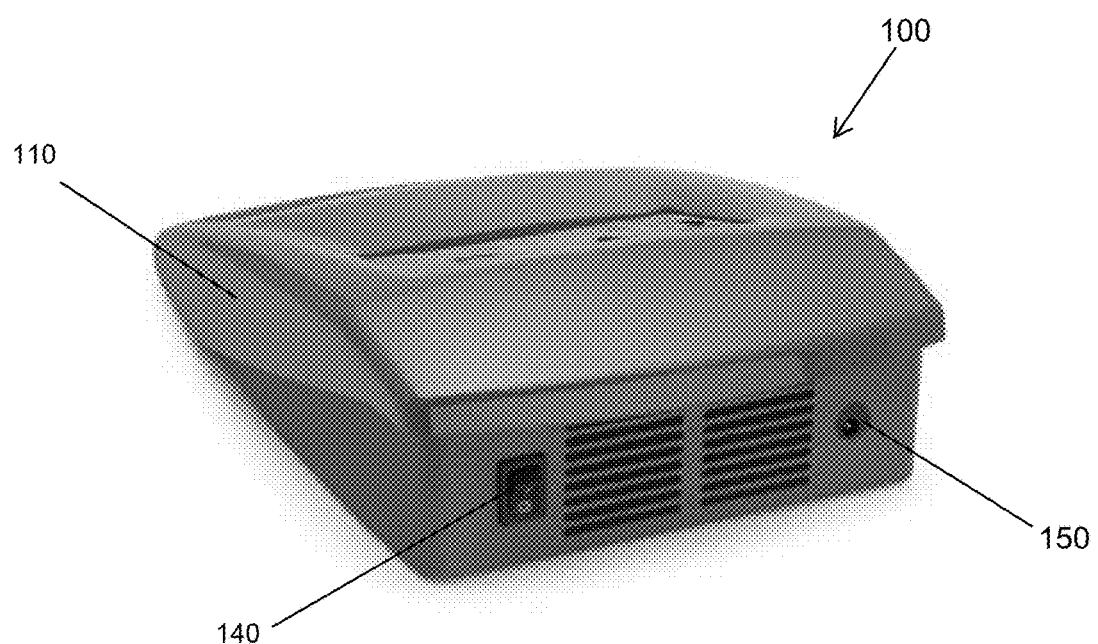
FIG. 2 depicts a back perspective view of the device of FIG. 1.

FIG. 2 depicts a back perspective view of the device 100 of FIG. 1A showing a power button 140 and a power input 150.

Figures 3, 4:
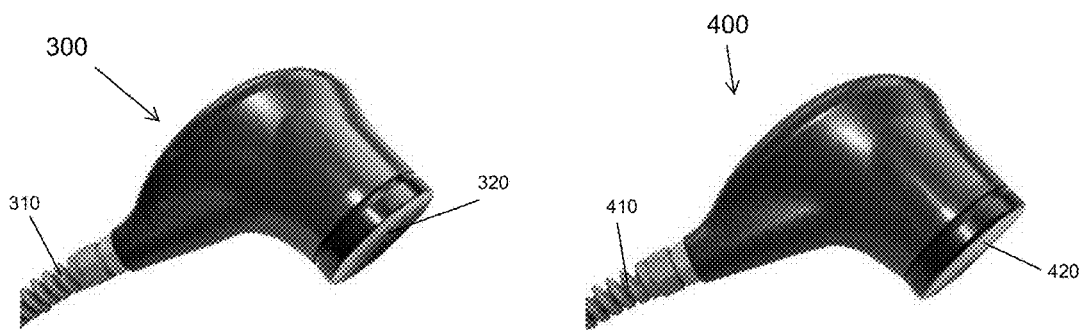
FIG. 3 depicts one embodiment of a hand probe, or transducer, having a concave contact surface.
FIG. 4 depicts one embodiment of a hand probe, or transducer, having a flat contact surface.

FIG. 3 depicts one embodiment of a hand probe, or transducer, having a concave contact surface. Hand probe 300 comprises a power cord 310 ending in a connector for supplying power from the main unit/generator 110 of FIG. 1A and a contact surface 320 comprising a concave contact surface. A piezoelectric element and a microchip (not shown) are contained within the hand probe 300. Electric current is supplied from main unit/generator 110 of FIG. 1A through power cord 310 to the piezoelectric elements, which change shape and vibrate, causing sound waves to travel outward comprising the ultrasound waves. In one embodiment, hand probe 300 comprises a plurality of piezoelectric elements, each having its own circuit and each operated independently of each other.

FIG. 4 depicts one embodiment of a hand probe, or transducer, having a flat contact surface. Hand probe 400 comprises a power cord 410 ending in a connector for supplying power from the main unit/generator 110 of FIG. 1A and a contact surface 420 comprising a flat contact surface. A piezoelectric element and a microchip (not shown) are contained within hand probe 400. Electric current is supplied from main unit/generator 110 of FIG. 1A through power cord 410 to the piezoelectric elements, which change shape and vibrate, causing sound waves to travel outward comprising the ultrasound waves. In one embodiment, hand probe 400 comprises a plurality of piezoelectric elements, each having its own circuit and each operated independently of each other.

Figure 5:
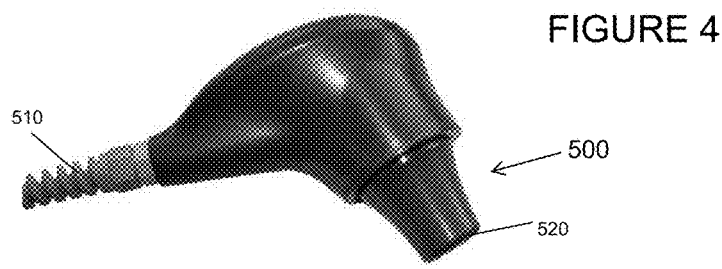
FIG. 5 depicts one embodiment of a hand probe, or transducer, having a small surface area flat contact surface.

FIG. 5 depicts one embodiment of a hand probe, or transducer, having a small surface area flat contact surface. Hand probe 500 comprises a power cord 510 ending in a connector for supplying power from the main unit/generator 110 of FIG. 1A and a contact surface 520 comprising a small surface area contact surface. A piezoelectric element and a microchip (not shown) are contained within the hand probe 500. Electric current is supplied from main unit/generator 110 of FIG. 1A through power cord 510 to the piezoelectric elements, which change shape and vibrate, causing sound waves to travel outward comprising the ultrasound waves. In one embodiment, hand probe 500 comprises a plurality of piezoelectric elements, each having its own circuit and each operated independently of each other.

Figure 6:
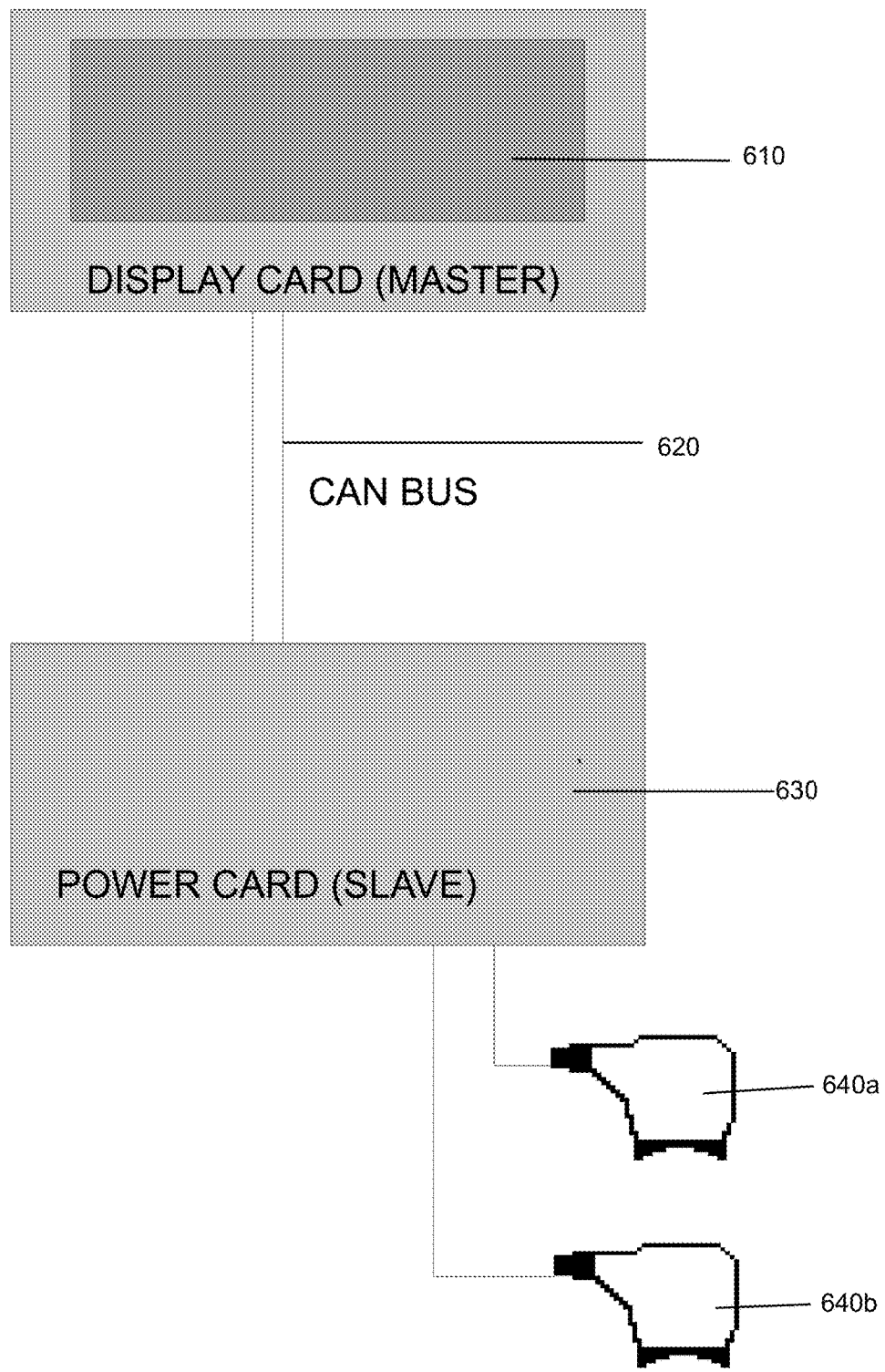
FIG. 6 depicts a flow diagram of the flow of information and control between the integrated printed circuit board assemblies according to one embodiment of the invention.

FIG. 6 depicts a flow diagram of the flow of information and control between the integrated printed circuit board assemblies according to one embodiment of the invention. The display integrated printed circuit board assembly 610 communicates over CAN bus 620 with power integrated printed circuit board assembly 630. Power integrated printed circuit board assembly 630 communicates and controls hand probes 640*a*, 640*b*.

Figure 7:
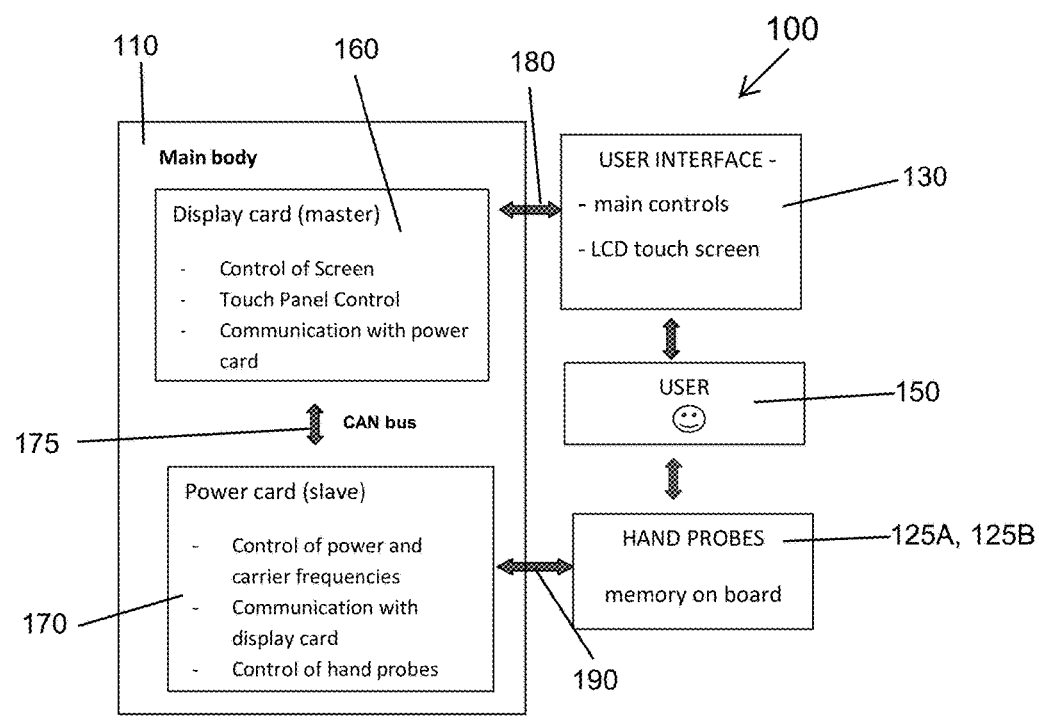
FIG. 7 depicts a flowchart depicting operation and control of the device.

FIG. 7 depicts operation and control of the device 100. The user 150 turns on the main unit/generator 110 at the touch-screen display 130. Display integrated printed circuit board assembly (master) 160 and power integrated printed circuit board assembly (slave) 170 are embedded in main unit/generator 110 and communicate via CAN bus 175. Display integrated printed circuit board assembly 160 communicates with display 130 via communication link 180. Power integrated printed circuit board assembly 170 communicates with hand probes 125*a*, 125*b* via communication link 190.

Figure 8:
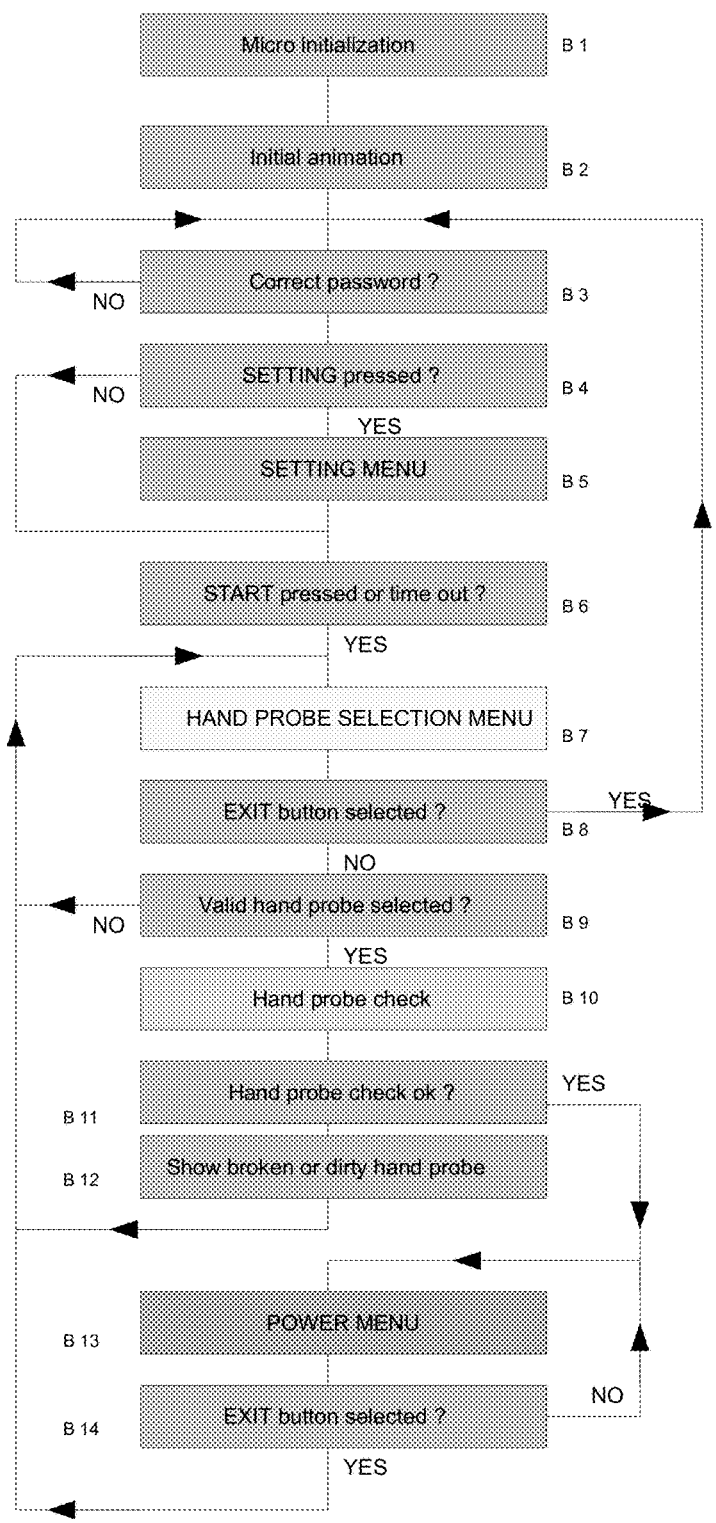
FIG. 8 depicts a flow diagram for the display integrated printed circuit board assembly according to one embodiment of the invention.
Figure 9:
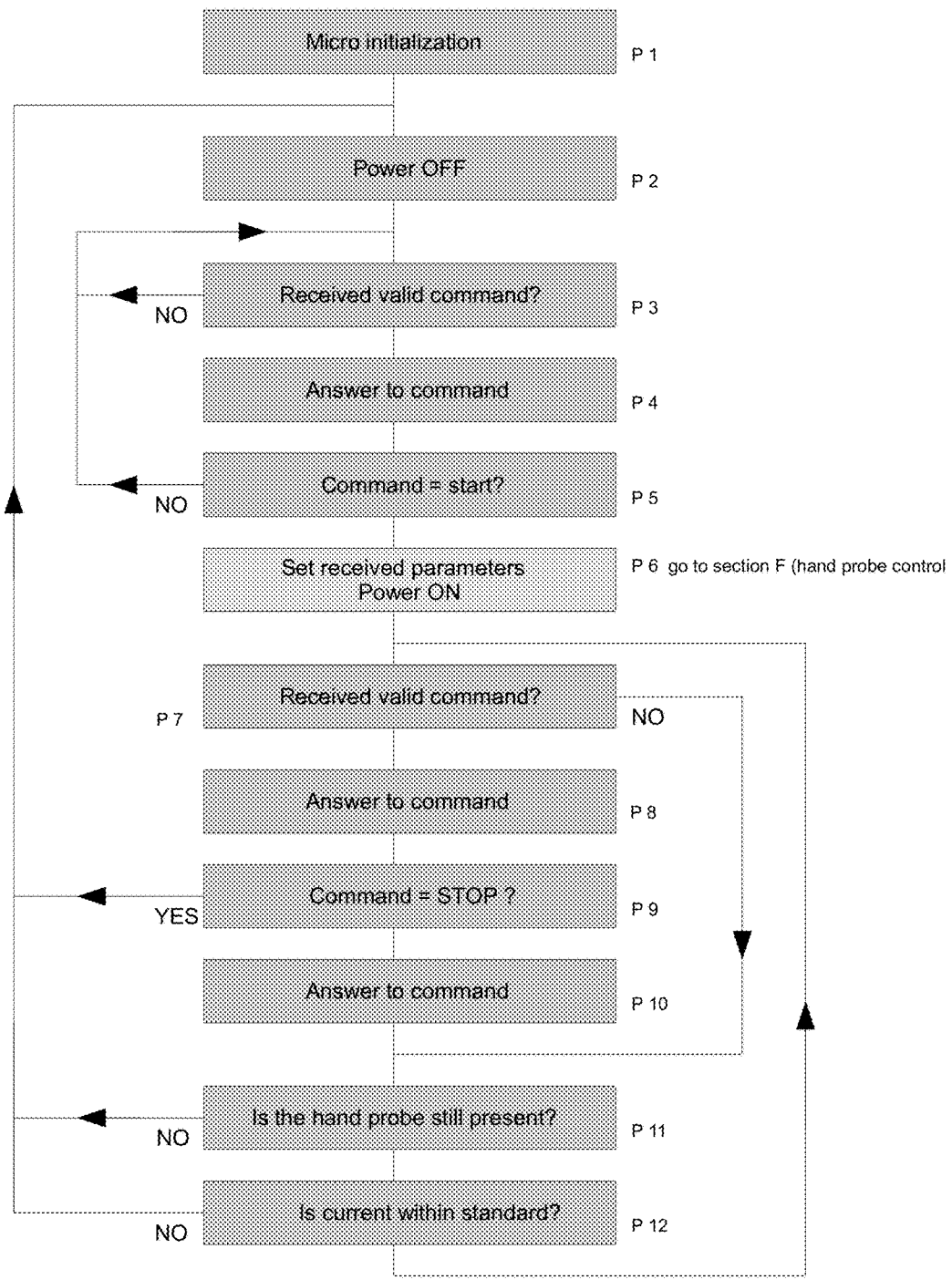
FIG. 9 depicts a flow diagram for the power integrated printed circuit board assembly according to one embodiment of the invention.

FIG. 8 depicts a flow diagram for the display printed circuit board assembly according to one embodiment of the invention. At B1, the display integrated printed circuit board assembly initializes. At B2 the display card is animated with the Start screen (see FIG. 14A) and the user enters a PIN. At B3, if a correct password (PIN) is entered, the user is presented with the working screen shown in FIG. 14C. If an incorrect password (PIN) is entered, the user is prompted to re-enter the PIN. Once the user enters the correct password (PIN) or PUK, the user can select SETTING or START at the working screen FIG. 14C. If SETTING is selected at B4, the user is presented with the SETTING menu screen FIG. 14D at B5. If no selection is made at the SETTING screen menu at B4 within a predetermined amount of time, or if the user selects START at the START menu at B6, the HAND PROBE SELECTION MENU, FIG. 11, is initiated at B7. If the user selects the EXIT button at B8, the user is returned to B3 to begin the process again. If the user does not select EXIT at B8, the user selects a hand probe and initiates the HAND PROBE SELECTION MENU, FIG. 11, at B9. If a valid hand probe is not selected, the user is returned to the HAND PROBE SELECTION MENU at B7. If a valid hand probe is selected at B9, the power integrated printed circuit board assembly initiates the HAND PROBE CHECK, FIG. 10, and conducts a safety check on the selected hand probe at B9. If the hand probe passes the safety check at B11, the POWER MENU, FIG. 9, is initiated. If the hand probe fails the safety check at B11, at B12 the user checks the hand probe to see if it is dirty or broken and attempts to repair any problem that can be fixed by the user. The user is then returned to B7 to check the hand probe. Once the hand probe passes the safety check, at B13 the POWER MENU is initiated. At B14, if the EXIT button is selected by the user, the HAND PROBE SELECTION MENU is presented. If the EXIT button at B14 is NOT selected, the POWER MENU is initiated.

FIG. 9 depicts a flow diagram for the power integrated printed circuit board assembly according to one embodiment of the invention. At P1, the power integrated printed circuit board assembly is initialized. At P2 the power to the device is off. At P3, when the power integrated printed circuit board assembly receives a valid command from the display integrated printed circuit board assembly, it answers at P4. If at P5 the command is START, at P6 the HAND PROBE CONTROL MENU is initiated at FIG. 10 where a safety check is run on the selected hand probe. Once the hand probe passes the safety check and the power integrated printed circuit board assembly receives a valid command at P7, it answers the command. If the command is STOP at P9, the power is turned off to the hand probe by the power integrated printed circuit board assembly. If the command is not STOP at P9, at P10 the power integrated printed circuit board assembly answers the command at P10 and determines if the hand probe is still present (connected to the device). If no, the power is turned off by the power integrated printed circuit board assembly. If the hand probe is still present at P11 the power integrated printed circuit board assembly determines if the current is within standard values for the hand probe at P12. If no, the power integrated printed circuit board assembly turns off the power to the hand probe. If yes, the power integrated printed circuit board assembly awaits a valid command from the display integrated printed circuit board assembly at P7.

Figure 10:
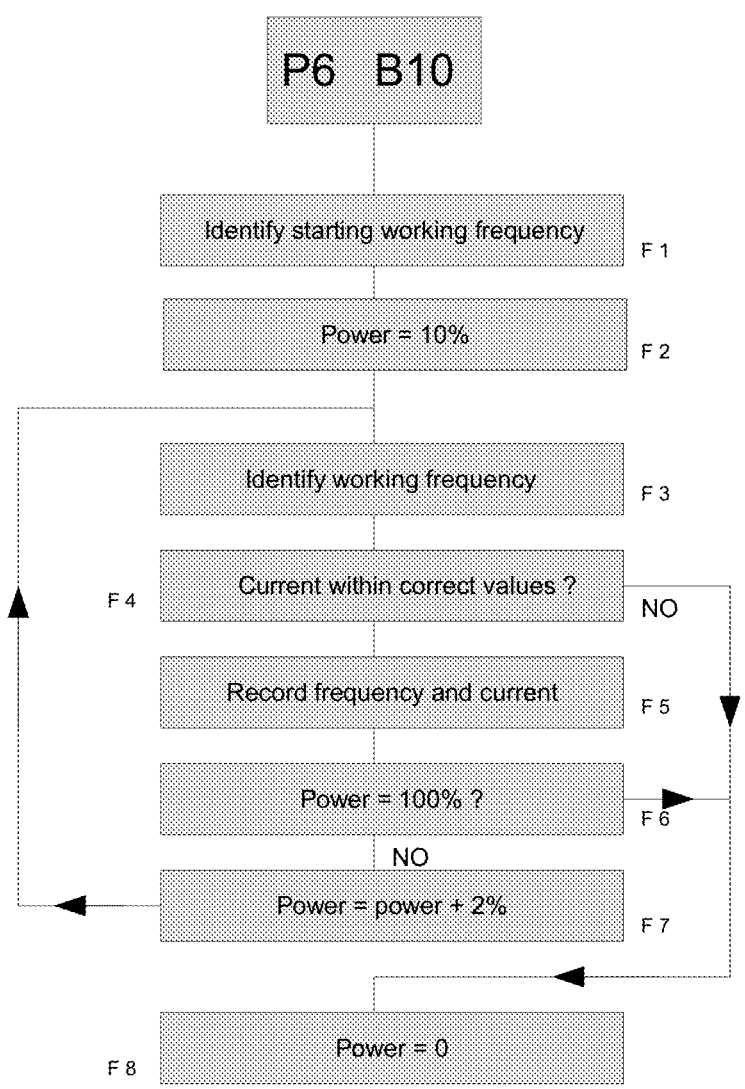
FIG. 10 depicts a functions block consisting of controls embedded in the firmware of the microprocessors of the integrated printed circuit board assemblies for the hand probe control command according to one embodiment of the invention.
Figure 11:
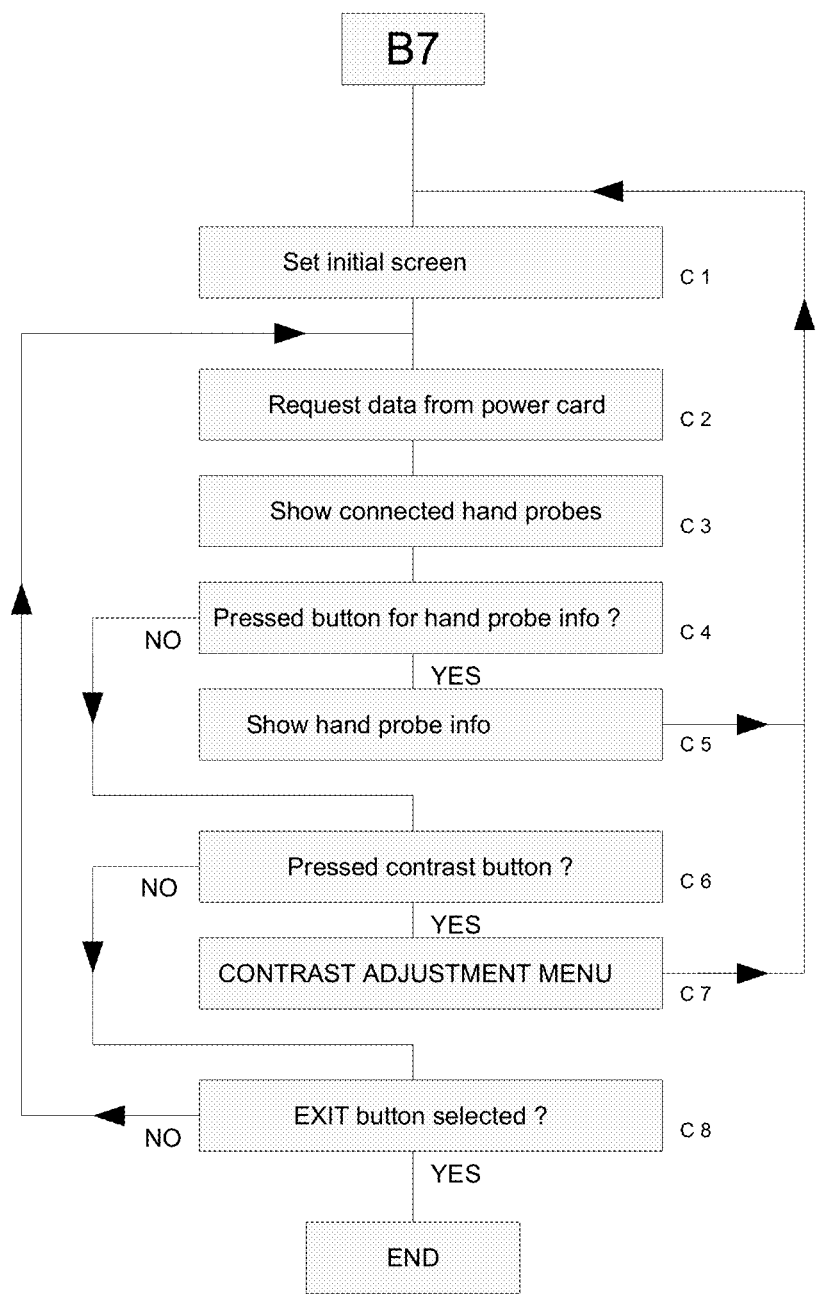
FIG. 11 depicts a functions block consisting of controls embedded in the firmware of the microprocessors of the integrated printed circuit board assemblies for the hand probe selection menu according to one embodiment of the invention.

FIG. 10 depicts a functions block consisting of controls embedded in the firmware of the microprocessors of the integrated printed circuit board assemblies for the hand probe control command according to one embodiment of the invention. The HAND PROBE CONTROL MENU is initiated at P6 of the power integrated printed circuit board assembly routine and also at B10 of the display integrated printed circuit board assembly routine. At F1, the starting working frequency is identified. At F2, the power is set to 10%. At F3, the working frequency of the hand probe is identified. At F4, if the hand probe readings correspond to correct values, at F5 the frequency and current are read and recorded by the power integrated printed circuit board assembly. At F5 and F6, the power is increased by increments of 2% until 100% power is reached. At each increment, the frequency and current are read and determined if they fall within correct values for the hand probe. Once the power reaches 100% at F6, the power is reduced to zero at F8.

FIG. 11 depicts a functions block consisting of controls embedded in the firmware of the microprocessors of the integrated printed circuit board assemblies for the hand probe selection menu according to one embodiment of the invention.

Figure 12:
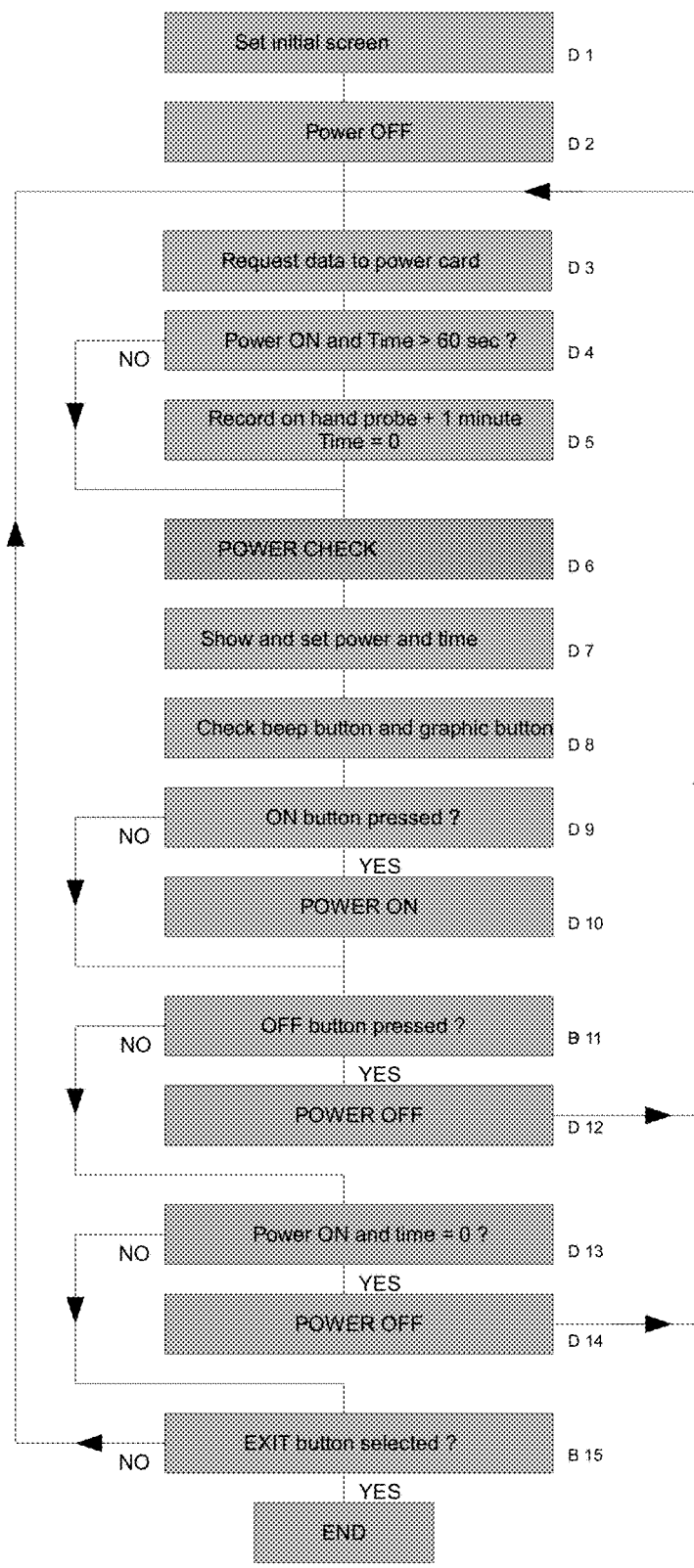
FIG. 12 depicts a functions block consisting of controls embedded in the firmware of the microprocessors of the integrated printed circuit board assemblies for the power menu according to one embodiment of the invention.

FIG. 12 depicts a functions block consisting of controls embedded in the firmware of the microprocessors of the integrated printed circuit board assemblies for the power menu according to one embodiment of the invention. The POWER MENU is initiated at B13 of FIG. 8. At D1, the initial screen is set and at D2 the power is off. At D3, a request for data is sent to the power integrated printed circuit board assembly. At D4, an inquiry is made whether the power is turned ON to the hand probe and the treatment time is set for >60 seconds. If NO, at D6 the POWER CHECK routine is initiated at FIG. 13. If yes, at D5 a record is made of the output of the hand probe after 1 minute has passed. At D6, the POWER CHECK routine is initiated at FIG. 13. Once the POWER CHECK routine is completed at D6, at D7 the user sets the power and time for treatment. At D8, the user checks and adjusts, if desired, the sound and the graphics of the display. At D9, the user presses the ON button to start the treatment. At D10, once the ON button is pressed, power is provided to the hand probes until the OFF button is pressed at B11. If the power button is pressed at B11, the power is cut off to the hand probe at D12. If the power button is not turned off until the treatment time=0 at D13, the power is then turned off at D14. If the power button is turned off before treatment time=0 at D13, the routine returns to D3 and another power check is run on the hand probe. If the treatment is finished, at B15 the user selects the END button and ends the treatment. If the EXIT button is not selected at B15, the routine returns to conduct another power check of the hand probe.

Figure 13:
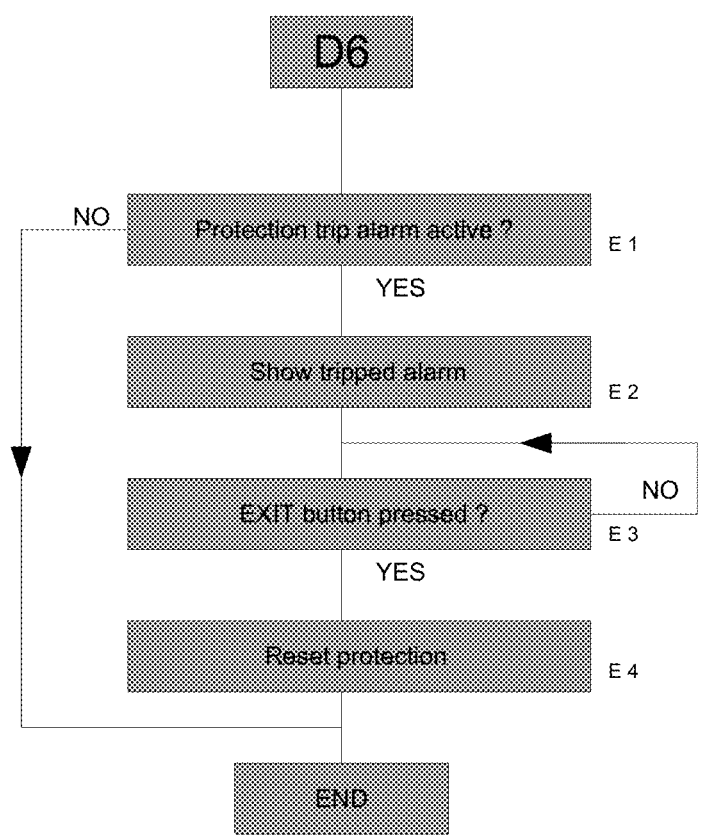
FIG. 13 depicts a functions block consisting of controls embedded in the firmware of the microprocessors of the integrated printed circuit board assemblies for the power control according to one embodiment of the invention.

FIG. 13 depicts a functions block consisting of controls embedded in the firmware of the microprocessors of the integrated printed circuit board assemblies for the power control according to one embodiment of the invention. The POWER CONTROL routine is initiated at D6 of the POWER MENU routine of FIG. 12. At E1, it is determined if the protection trip alarm is active. If yes, the tripped alarm is displayed at E2. At E3, once the EXIT button is pressed by the user, the protection trip alarm is reset at E4. If at E1 the protection trip alarm is not active, the routine is ended and returns to D6 of the POWER CONTROL routine.

Figure 14A:
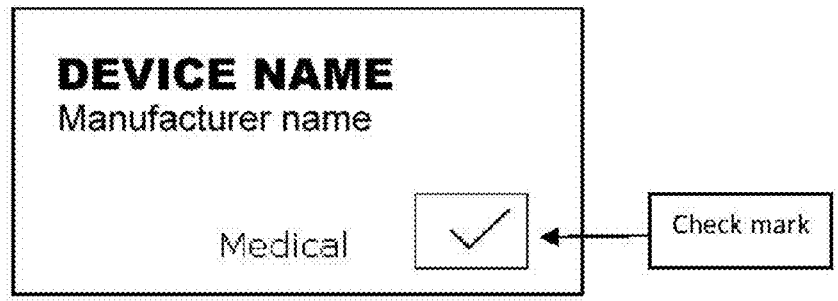
FIGS. 14A-Q depict a series of screenshots from the display showing implementation of software design specifications to provide functionalities according to one embodiment of the invention.
Figure 14B:
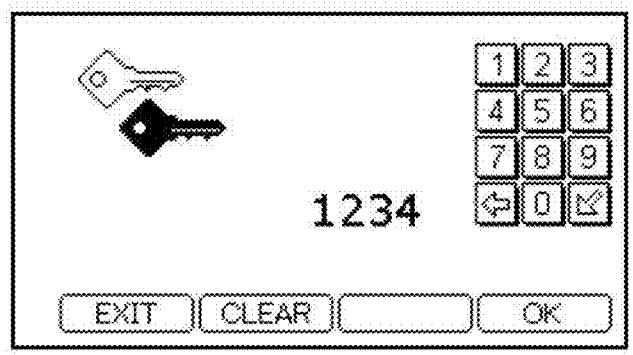
Figure 14C:
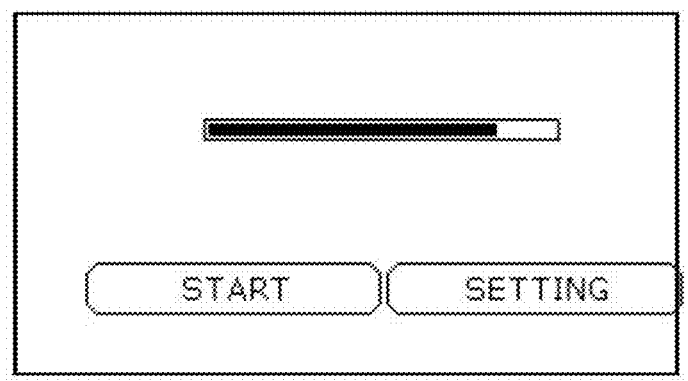
Figure 14D:
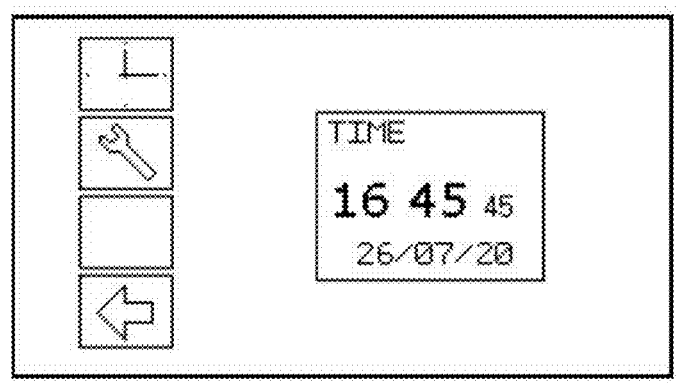
Figure 14E:
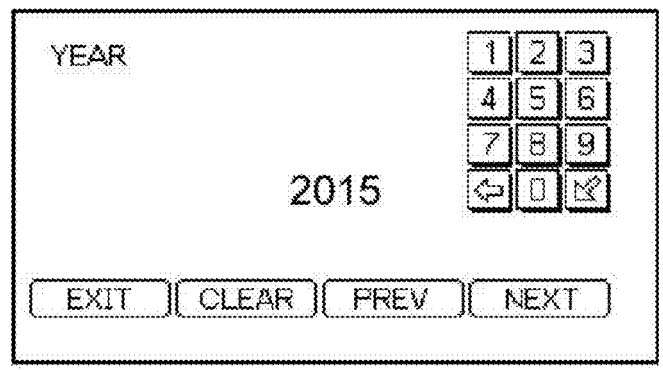
Figure 14F:
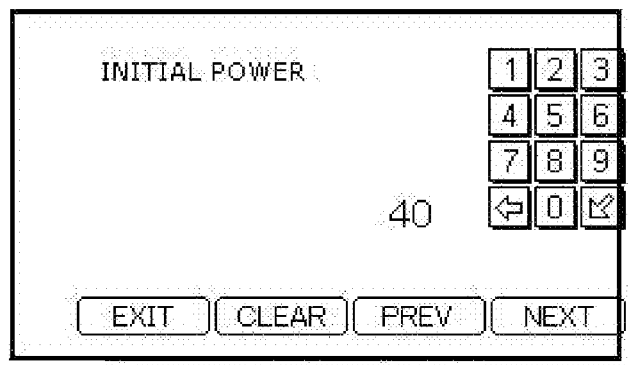
Figure 14G:
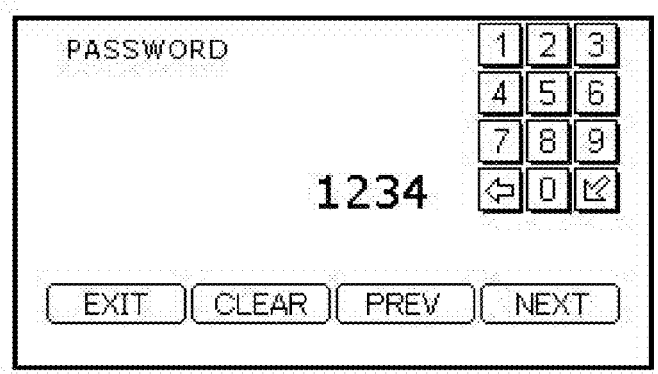
Figure 14H:
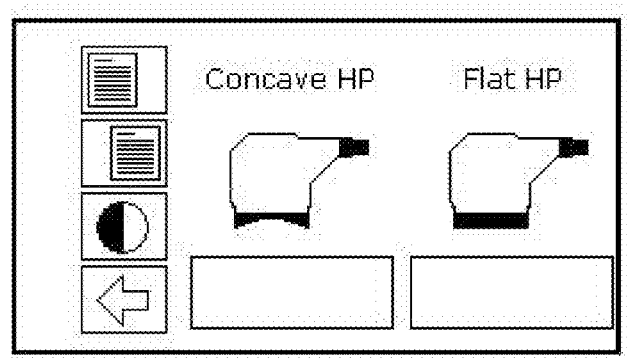
Figure 14I:
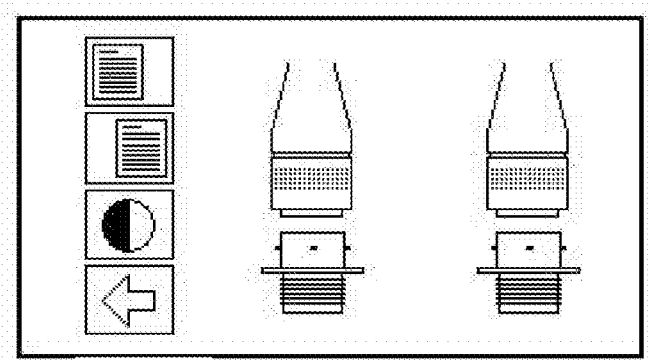
Figure 14J:
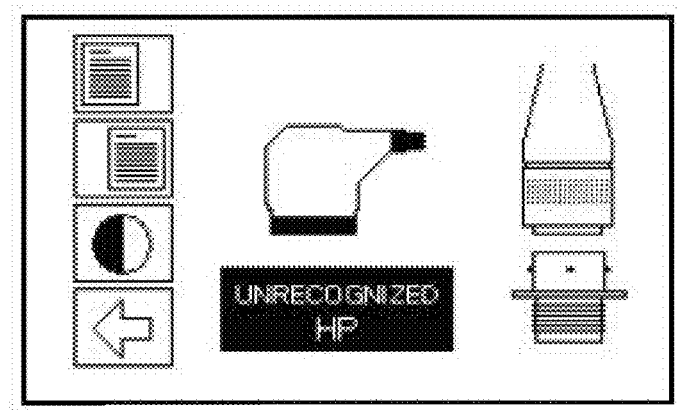
Figure 14K:
Figure 14L:
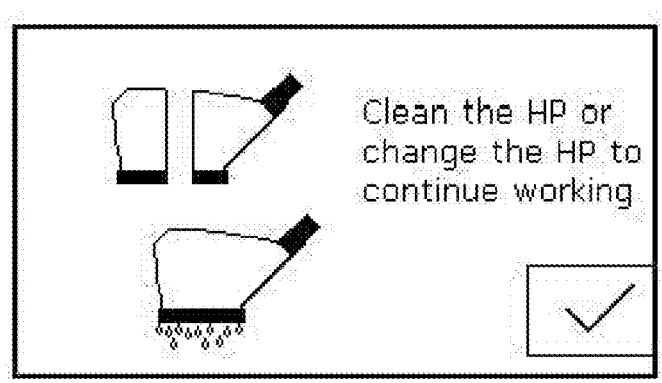
Figure 14M:
Figure 14N:
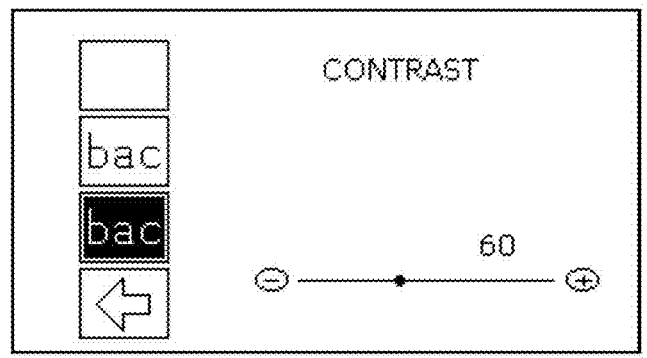
Figure 14O:
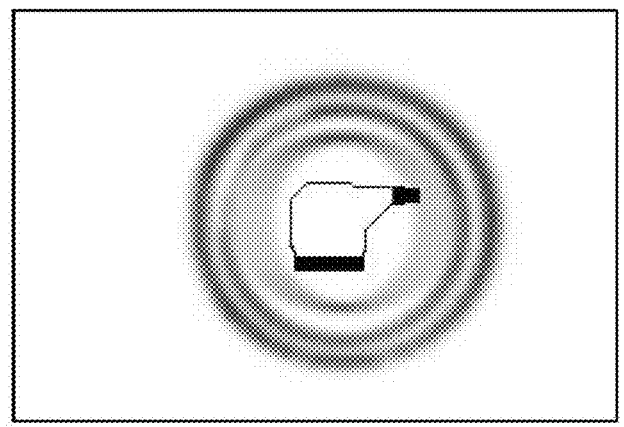
Figure 14P:
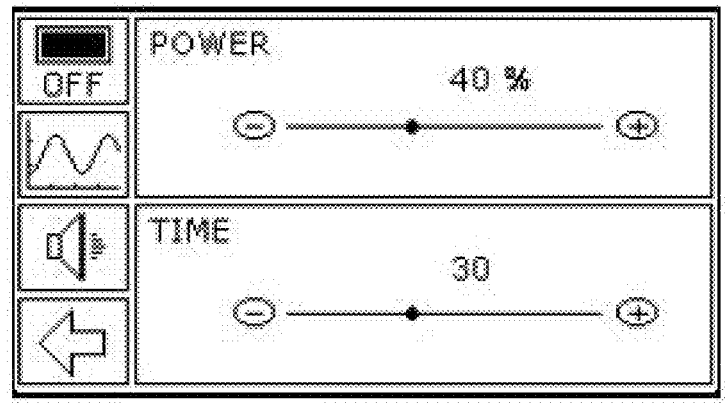
Figure 14Q:
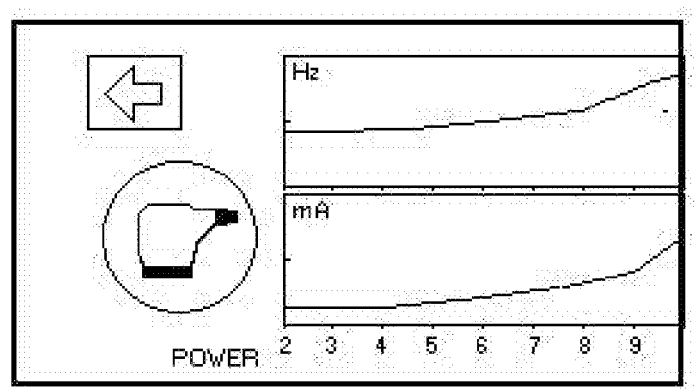

FIGS. 14A-Q depict a series of screenshots of the display showing implementation of software design specifications to provide functionalities according to one embodiment of the invention. FIG. 14A depicts the start screen which appears after power to the device is turned on. FIG. 14B depicts one method of security requiring entry of a PIN number on the display to proceed. The user may be given an opportunity to enter a PUK code if he/she cannot remember the PIN code. The PUK code is programmed into the software and cannot be modified. Once the correct PIN or PUK code is entered, the working screen shown in FIG. 14C appears. The user may push START and proceed to the START screen in FIG. 14H.

It is also possible to check and/or modify predetermined settings by pressing SETTING in FIG. 14C. If no selection is made during a predetermined amount of time after pressing SETTING, the START screen of FIG. 14H will appear. If the user elects SETTINGS at FIG. 14C, the setting menu screen of FIG. 14D appears where several menu items are provided for performing tasks. If the user elects to set date and time, FIG. 14E appears. Once the user is finished or elects not to change the date and time, he/she presses EXIT to return to FIG. 14D. The user can elect to change hand probe power output and treatment duration at the beginning or during the treatment session in which case FIG. 14F appears. When the user is done, pressing EXIT returns the user to FIG. 14D. If the user elects to change the PIN code, FIG. 14G appears. When finished, pressing EXIT returns the user to FIG. 14D. The user can then exit from the setting screen of FIG. 14D and be taken to the START screen of FIG. 14H.

At the START screen at FIG. 14H, the user is presented with information on connected hand probes as detected by the device upon startup or after attachment of one or more hand probes. While multiple hand probes can be connected and detected, the user must select one for a treatment. If no hand probes are detected as connected to the device, the screen at FIG. 14I appears which invites the user to connect one or more hand probes. If the device does not recognize a hand probe (i.e. no information is stored in the memory of the power printed circuit board assembly that is associated with a detected hand probe and the information stored in the IC chip in the hand probe by the manufacturer), FIG. 14J appears advising the user that the device does not recognize one or more of the hand probes. The device will not operate with a hand probe that is not recognized by the device.

From either of FIG. 14I and FIG. 14J, the user must exit to return to FIG. 14H. When the user selects a recognized hand probe from the display screen, a dialogue box appears which informs the user of the hours left for treatment using the selected hand probe. When 20 hours or less remain, FIG. 14K appears that provides a warning to the user of the remaining time for treatment. The device will not operate with a hand probe selected where all treatment hours have expired.

Each time a hand probe is selected at FIG. 14H, the device performs a safety check of the selected hand probe. If the device detects an issue that needs to be resolved, FIG. 14L will appear and inform the user of elections to continue the treatment. For example, the selected hand probe may need cleaning. In some instances, certain repairs of hand probes can only be made by the manufacturer in which case the user may be informed to select another hand probe. The device will not operate a treatment with a hand probe that has an issue that is not resolvable by the user. The user must check a box in this screen confirming that the message has been read, and then return to FIG. 14H.

From FIG. 14H, the user can select to review features of the connected hand probes displayed at FIG. 14M. The user can exit FIG. 14M by checking a box, or otherwise exiting the screen. From FIG. 14H, the user can also elect to adjust the display such as contrast and color. In that case, FIG. 14N appears allowing the user to make the desired changes, and then return to FIG. 14H.

To start treatment, the user presses on the image of the selected hand probe and FIG. 14O appears while the device checks the status of the hand probe. The hand probe features screen FIG. 14M then appears. The user must check the box or otherwise exit the hand probe features screen to start the treatment. The treatment screen FIG. 14P then appears which displays the hand probe power (percentage of power) and treatment duration (time). To start treatment, the user selects ON, at which time the icon changes to read OFF. During treatment, the user can adjust the power and/or time by sliding the indicator on the respective scales on the screen. Power and time can also be increased or decreased by pressing the + or − buttons at either end of the scales. When the timer reaches 0, the hand probe stops working and the display returns to FIG. 14H.

At any time during treatment, the user can elect to view two diagrams in FIG. 14Q showing frequency variation (Hz) according to the power set for the treatment and electric current intensity (mA) according to the hand probe power. The diagrams measure the hand probe performance which should follow a certain pattern; if the hand probe incurs a mechanical failure, it will lose power before expiration of the treatment time assigned by the manufacturer and a second line will appear on each diagram showing the measured frequency variation and electric current intensity.

At the treatment screen FIG. 14P, the user can turn sound effects on and off by selecting a speaker icon.

When treatment is finished, the device returns to FIG. 14H. The user can then select the other hand probe if the treatment plan so requires. If the user elects to exit, he/she will be taken back to the starting screen FIG. 14A and either turn off the device, or begin the process for a new treatment.

Figure 15:
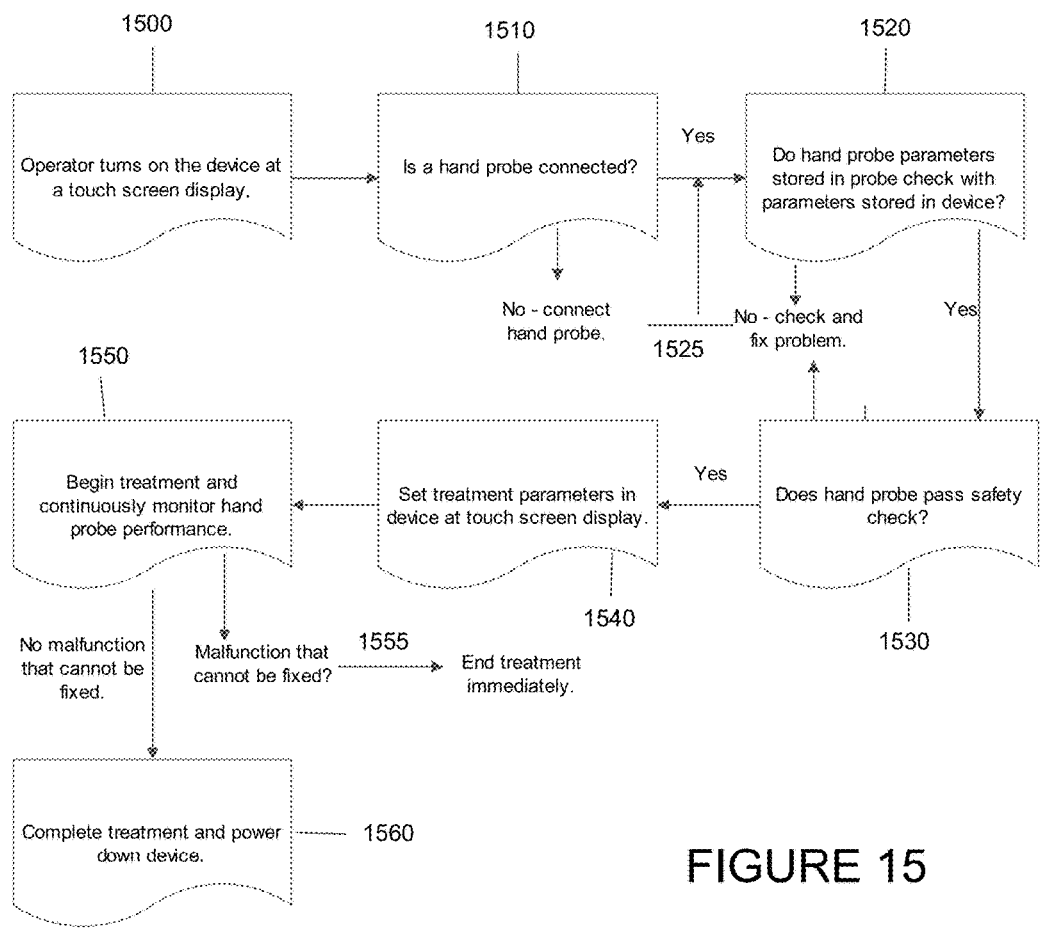
FIG. 15 depicts a flowchart operation of the device according to one embodiment of the invention.

FIG. 15 provides a flowchart of the operation of the device. At 1500, an operator turns on the device at a touch screen display which may require a security clearance, such as entry of a PIN. Upon start up, at 1510 the display printed circuit board assembly inquires whether a hand probe is connected. If yes, at 1520 the power integrated printed circuit board assembly checks the hand probe parameters that are stored in a microchip in the hand probe by the manufacturer with preloaded information stored in the memory of the device. If no, at 1525 the operator attaches at least one hand probe which is then tested to see if the parameters are consistent with the parameters stored in the device memory for that type and brand of hand probe. If the hand probe parameters fall within predetermined specifications such as remaining time of operation, at 1530, the operator can select which hand probe to use for treatment and the main unit/generator conducts a safety check of the hand probe by acquiring data relative to the hand probe's performance. For example, in one embodiment, the selected hand probe is brought between 10% and 100% of its nominal power in 2% increments and its performance is measured for 40 data points. If the hand probe passes the safety check, at 1540 treatment, parameters such as power output and time of operation are set in the device by the operator at the touchscreen display, or preset treatment parameters that have been stored in memory are recalled. If the hand probe fails the safety check, at 1525 the operator analyzes the problem to see if it can be fixed to continue to the treatment screen on the touchscreen display. If not, the treatment cannot be accessed. At 1550, treatment begins by providing power to the hand probe wherein the operator starts the treatment session by pressing the "On" button of the touch-screen display on the treatment screen. During treatment, performance of the hand probe is monitored constantly by the device and compared to predetermined safety values such as amperage drawn by the hand probe. If a deviation that exceeds preset safety values is determined by the main unit/generator, such as excessive power draw by the hand probe, the device shuts down at 1555 and an alarm is sounded. If no problem arises during treatment, at 1560, the treatment is completed and the device is powered down.

The foregoing embodiments have been presented for the purpose of illustration and description only and are not to be construed as limiting the scope of the invention in any way.

What is claimed is:

1. A low frequency ultrasound device comprising:
a main unit;
two hand probe connection inputs; and
two hand probes each comprising a power cord and a power cord connector connected to the main unit; and
wherein the main unit comprises a display comprising information regarding one or both hand probes, a treatment protocol and performance parameters of the main unit,
wherein the main unit further comprises a first printed circuit board assembly and a second printed circuit board assembly, wherein the first printed circuit board assembly and the second printed circuit board assembly share information via a CAN BUS protocol, wherein the first printed circuit board assembly comprises a display circuit board assembly, wherein the second printed circuit board assembly comprises a power circuit board assembly, wherein the power circuit board assembly responds to requests for information from the display circuit board assembly, wherein each of the first printed circuit board assembly and the second printed circuit board assembly comprises a printed circuit board and one or more of resistors, capacitors, transistors, diodes, amplifiers, resistor arrays, logic gates, semiconductors, clocks, switches, microprocessors and memory and combinations thereof, wherein the second printed circuit board assembly is programmed to regulate if amperage is sent to the hand probes and how much amperage is send to the hand probes,
wherein each hand probe comprises an integrated circuit chip with readable memory and at least one piezoelectric element, and a contact surface, wherein the hand probe receives power via the power cord from the main unit as regulated by the second printed circuit board assembly, wherein each hand probe further comprises one sonotrode disposed at one end of the piezoelectric element and a steel plate disposed at the opposite end from the sonotrode of the piezoelectric element,
wherein information is stored in the hand probe by its manufacturer comprising hand probe manufacturer information, hand probe calibration information, emission type comprising continuous or pulsed, duty cycle, hand probe frequency parameters and treatment hours assigned to the hand probe,
wherein the power circuit board assembly is in communication with the hand probe,
wherein hand probe performance information as determined by the manufacturer is stored in the memory of the main unit, wherein the low frequency ultrasonic device operates at about 20 KHz to about 100 KHz.

2. The low frequency ultrasound device of claim 1 wherein the requests from the display circuit board assembly to the power circuit board assembly comprise hand probe manufacturer information stored in the integrated circuit chip inside each hand probe by its manufacturer, calibration information of each hand probe, emission type of each hand probe, duty cycle of each hand probe, power status of each hand probe, hand probe frequency parameters and treatment hours assigned to each hand probe.

3. The low frequency ultrasound device of claim 2 wherein a maximum number of treatment hours is assigned to the hand probe and stored in the readable memory of the device, wherein the maximum number of treatment hours assigned to the hand probe is compared to an actual total treatment hours for that hand probe that has been stored in the memory of the main unit of the device, wherein if the actual total treatment hours for the hand probe is within twenty treatment hours of or exceed the maximum number of treatment hours assigned to the hand probe, power to the hand probe is cut-off by the main unit.

4. The low frequency ultrasound device of claim 1 wherein the power circuit board assembly conducts a test of a performance of each hand probe, wherein the performance test comprises bringing each hand probe to between about 10% and 100% of its nominal power in 2% power increments and measuring 40 data points, wherein the second printed circuit board measures the amperage demand by the hand probe for each data point.

5. The low frequency ultrasound device of claim 4 wherein power is cut to the hand probe by the main unit if the amperage demand by the hand probe as measured by the second printed circuit board exceeds a maximum amperage for the hand probe as stored in the integrated circuit of the hand probe by the manufacturer.

6. The low frequency ultrasound device of claim 3 further comprising an alarm, wherein the alarm is activated if power to the hand probe is cut-off by the main unit.

7. The low frequency ultrasound device of claim 5 further comprising an alarm, wherein the alarm is activated if power to the hand probe is cut-off by the main unit.

8. The low frequency ultrasound device of claim 7 wherein the alarm is a visual alarm, an audible alarm or a combination thereof.

9. The low frequency ultrasound device of claim 6 wherein the alarm is a visual alarm, an audible alarm or a combination thereof.

10. The low frequency ultrasound device of claim 5 wherein amperage demand by the hand probe as measured by the second printed circuit board exceeds the maximum amperage for the hand probe as stored in the integrated circuit of the hand probe by the manufacturer due to the material on which the hand probe transducer contact surface is in contact.

11. The low frequency ultrasound device of claim 1 wherein a failure in either the hardware or the software results in a cut of power to each hand probe.

12. The low frequency ultrasound device of claim 1 wherein the transducer contact surface shape comprises flat, concave or convex.

13. The low frequency ultrasound device of claim 1 further comprising a security feature that must be entered on the display to operate the main unit.

14. The low frequency ultrasound device of claim 1 wherein a treatment protocol is programmed using the display unit, the treatment protocol comprising a time value and a power value, wherein the power circuit board assembly controls operation of each hand probe according to the treatment protocol.

15. The low frequency ultrasound device of claim 14 wherein the treatment protocol further comprises continuous or pulsed emission, wherein the treatment protocol further comprises different duty cycles.

16. The low frequency ultrasound device of claim 1 wherein the display indicates a history of each hand probe, wherein the history comprises a number of hours or treatment left for the hand probe under the manufacturer's guidelines.

17. An ultrasonic aesthetic treatment method comprising:
operating a touch screen display to turn on power to the main unit of an ultrasonic device;
conducting an inquiry to determine if one or more hand probes are attached to the ultrasonic device;
comparing the performance parameters of each hand probe according to stored information in a memory of the main unit to performance parameters that are stored within an integrated circuit chip disposed in each hand probe and programmed with hand probe parameters by the manufacturer of the hand probe, wherein the performance parameters comprise a maximum amperage for the hand probe as stored in the integrated circuit of the hand probe by the manufacturer;
reading from the memory of the main unit a maximum number of treatment hours assigned to each hand probe and reading from the memory of the main unit an actual number of treatment hours that each hand probe has been used;
thereafter if the actual number of treatment hours for each hand probe as stored in the memory unit of the main device are less than twenty hours of the maximum number of treatment hours assigned to each hand probe, thereafter conducting a performance test of each hand probe, wherein the performance test comprises bringing each hand probe to between about 10% and 100% of its nominal power in 2% power increments and measuring 40 data points, wherein the amperage demand by the hand probe is measured for each data point;
wherein if the amperage demand by each hand probe as measured does not exceed the maximum amperage for the hand probe as stored in the integrated circuit of the hand probe by the thereafter setting aesthetic treatment protocol parameters using the touch screen display;
wherein if the amperage demand by either hand probe as measured exceeds the maximum amperage for the hand probe as stored in the integrated circuit of the hand probe by the manufacturer thereafter cleaning the hand probe by the operator,
wherein if the hand probe is cleaned by the operator such that its performance test compares favorably to the maximum amperage for the hand probe as stored in the integrated circuit of the hand probe by the manufacturer, thereafter setting aesthetic treatment protocol parameters using the touch screen display;
thereafter providing power to one of the hand probes; and
continuously monitoring the performance of each hand probe for the actual number of treatment hours and the amperage demand, wherein if either of the actual number of treatment hours and the amperage demand exceed the assigned values, power is thereafter discontinued to the hand probe, wherein if both of the actual number of treatment hours and the amperage demand for each hand probe do not exceed the values assigned to each hand probe the aesthetic treatment protocol is completed, wherein the ultrasonic device comprises the device of claim 1.

18. An ultrasonic therapeutic treatment method comprising:

operating a touch screen display to turn on power to the main unit of an ultrasonic device;

conducting an inquiry to determine if one or more hand probes are attached to the ultrasonic device;

comparing the performance parameters of each hand probe according to stored information in a memory of the main unit to performance parameters that are stored within an integrated circuit chip disposed in each hand probe and programmed with hand probe parameters by the manufacturer of the hand probe, wherein the performance parameters comprise a maximum amperage for the hand probe as stored in the integrated circuit of the hand probe by the manufacturer;

reading from the memory of the main unit a maximum number of treatment hours assigned to each hand probe and reading from the memory of the main unit an actual number of treatment hours that each hand probe has been used;

thereafter if the actual number of treatment hours for each hand probe as stored in the memory unit of the main device are less than twenty hours of the maximum number of treatment hours assigned to each hand probe, thereafter conducting a performance test of each hand probe, wherein the performance test comprises bringing each hand probe to between about 10% and 100% of its nominal power in 2% power increments and measuring 40 data points, wherein the amperage demand by the hand probe is measured for each data point;

wherein if the amperage demand by each hand probe as measured does not exceed the maximum amperage for the hand probe as stored in the integrated circuit of the hand probe by the manufacturer thereafter setting therapeutic treatment protocol parameters using the touch screen display;

wherein if the amperage demand by either hand probe as measured exceeds the maximum amperage for the hand probe as stored in the integrated circuit of the hand probe by the manufacturer thereafter cleaning the hand probe by the operator, wherein if the hand probe is cleaned by the operator such that its performance test compares favorably to the maximum amperage for the hand probe as stored in the integrated circuit of the hand probe by the manufacturer, thereafter setting therapeutic treatment protocol parameters using the touch screen display;

thereafter providing power to one of the hand probes; and continuously monitoring the performance of each hand probe for the actual number of treatment hours and the amperage demand, wherein if either of the actual number of treatment hours and the amperage demand exceed the values assigned to each hand probe, power is thereafter discontinued to the hand probe, wherein if both of the actual number of treatment hours and the amperage demand for each hand probe do not exceed the values assigned to each hand probe the therapeutic treatment protocol is completed, wherein the ultrasonic device comprises the device of claim 1.

\* \* \* \* \*